United States Patent
Sammohi et al.

(10) Patent No.: US 8,454,993 B2
(45) Date of Patent: Jun. 4, 2013

(54) CONTROLLED RELEASE PHARMACEUTICAL COMPOSITIONS OF PREGABALIN

(75) Inventors: Rahul Manorajan Sammohi, Pune (IN); Nikhil Prabhakar Malewar, Pune (IN); Makarand Krishnakumar Avachat, Pune (IN)

(73) Assignee: Lupin Limited, Mumbai (IN)

( * ) Notice: Subject to any disclaimer, the term of this patent is extended or adjusted under 35 U.S.C. 154(b) by 233 days.

(21) Appl. No.: 12/744,477

(22) PCT Filed: Nov. 14, 2008

(86) PCT No.: PCT/IN2008/000770
§ 371 (c)(1),
(2), (4) Date: May 24, 2010

(87) PCT Pub. No.: WO2009/066325
PCT Pub. Date: May 28, 2009

(65) Prior Publication Data
US 2010/0255067 A1    Oct. 7, 2010

(30) Foreign Application Priority Data
Nov. 23, 2007    (IN) .................. 1593/KOH/2007

(51) Int. Cl.
*A61K 9/14*    (2006.01)
*A61K 9/20*    (2006.01)
*A61K 9/48*    (2006.01)

(52) U.S. Cl.
USPC .................. 424/451; 424/464; 424/489

(58) Field of Classification Search
None
See application file for complete search history.

(56) References Cited

U.S. PATENT DOCUMENTS

| | | |
|---|---|---|
| 2002/0012679 A1 | 1/2002 | Bruna et al. |
| 2007/0264346 A1 | 11/2007 | Guimberteau et al. |
| 2009/0082466 A1 | 3/2009 | Babul |

FOREIGN PATENT DOCUMENTS

| | | |
|---|---|---|
| EP | 1591107 | 11/2005 |
| WO | WO 2006/008640 | 1/2006 |
| WO | WO 2006/078811 | 7/2006 |
| WO | WO 2008/140460 | 11/2008 |
| WO | WO 2009/066325 | 5/2009 |

OTHER PUBLICATIONS

International Search Report attached to WO 2009/066325.

*Primary Examiner* — Carlos Azpuru
(74) *Attorney, Agent, or Firm* — Frank Rosenberg

(57) ABSTRACT

A controlled release pharmaceutical composition which comprises therapeutically effective amount of pregabalin or salts thereof as active ingredient, a hydrophobic release controlling agent(s) and optionally other pharmaceutically acceptable excipients thereof.

6 Claims, 1 Drawing Sheet

CONTROLLED RELEASE PHARMACEUTICAL COMPOSITIONS OF PREGABALIN

This application is a national stage filing and claims the priority benefit of PCT/IN2008/000770 filed 14 Nov. 2008, and also claims the benefit of priority from provisional Indian patent application ser. no. 1593/KOL/2007, which was filed on 23 Nov. 2007.

FIELD OF THE INVENTION

The present invention relates to controlled release pharmaceutical compositions comprising pregabalin or salts thereof using hydrophobic rate controlling components.

BACKGROUND OF THE INVENTION

Pregabalin is an analog of gamma-aminobutyric acid (GABA). It is useful as antiseizure therapy for central nervous system disorders such as epilepsy, Huntington's chorea, cerebral ischemia, Parkinson's disease, tardive dyskinesia, and spasticity.

Pregabalin or (S)-(+)-3-(amino methyl)-5-methylhexanoic acid, binds to the alpha-2-delta ($\alpha$-$\delta$) subunit of a calcium channel and is related to the endogenous inhibitory neurotransmitter [$\gamma$] amino butyric acid (GABA), which is involved in the regulation of brain neuronal activity. Pregabalin exhibits anti-seizure activity and is useful for treating, among other conditions, epilepsy, pain, physiological conditions associated with psychomotor stimulants, inflammation, gastrointestinal damage, alcoholism, insomnia, fibromyalgia, and various psychiatric disorders, including anxiety, depression, mania, and bipolar disorder.

Pregabalin was approved in the United States on Dec. 30, 2004, an immediate release dosage form for use in the treatment of diabetic peripheral neuropathy, postherpetic neuralgia, and as an adjunctive treatment for partial onset seizures in adults.

Pregabalin is currently available as immediate release Lyrica® in 25, 50, 75, 100, 150, 200, 225, and 300 mg hard shell capsules and is administered in patients two or three times daily (BID or TID).

The recommended dose of pregabalin is 100 mg three times a day (300 mg/day) for the treatment of neuropathic pain associated with diabetic peripheral neuropathy and post herpetic neuralgia. Pregabalin at doses of 150 to 600 mg/day is recommended for adjunctive therapy for adult patients with partial onset seizures.

To maintain reasonably stable plasma concentrations, it is necessary to resort to frequent dosing, and the resulting inconvenience to the patient often results in lowered compliance with the prescribed dosing regimen. Moreover, widely fluctuating plasma concentrations of the drug may result in administration of less than therapeutic amounts of the drug in a conservative dosing regimen, or amounts too large for the particular patient in an aggressive dosing regimen.

This type of multiple administrations leads to substantial fluctuations in the plasma concentration of the drug, especially in chronic administration.

The convenience of once daily dosing generally improves patient compliance, especially for elderly patients and for patients taking multiple medications. Once per day dosing may also lessen or prevent potentially undesirable dose-related effects by reducing peak blood levels ($C_{max}$) and may also increase drug efficacy by increasing minimum plasma concentrations ($C_{min}$).

Once daily dosing of pregabalin, however, presents numerous challenges as pregabalin is not absorbed uniformly in the gastrointestinal (GI) tract. Pregabalin is absorbed in the small intestine and in the ascending colon in humans.

Various approaches have been tried out for developing a once daily dosage form of pregabalin.

WO 2007/052125 A2 relates to a pharmaceutical composition comprising pregabalin, and matrix forming agent and a swelling agent, the matrix-forming agent comprising polyvinyl acetate and polyvinylpyrrolidone, and the swelling agent comprising cross-linked polyvinylpyrrolidone, wherein the pharmaceutical composition is adapted for once-daily oral dosing.

US 2005/0163848 A1 relates to a complex comprised of pregabalin and a transport moiety, such as an alkyl sulfate. The complex has an enhanced absorption in the gastrointestinal tract, particularly the lower gastrointestinal tract. The complex, and compositions and dosage forms prepared using the complex, provide for absorption by the body of the drug through a period of ten to twenty-four hours, thus enabling a once-daily dosage form for pregabalin.

US 2002/0119197 A1 relates to pharmaceutical dosage form comprising a central core including a pharmaceutical agent in a controlled-release composition, said core having two exposed opposite end surfaces and a peripheral surface at an outer edge of said core extending between said two opposed end surfaces, said peripheral edge surrounded by a diffusion-limiting sleeve, wherein said sleeve limits the diffusion of fluids into said core.

Pregabalin is a white to off-white, crystalline solid with a $pK_{a1}$ of 4.2 and a $pK_{a2}$ of 10.6. It is freely soluble in water and both basic and acidic aqueous solutions.

Most of the above-mentioned patent applications disclose controlled delivery systems, which utilize hydrophilic, polymeric matrices. However, for highly soluble drugs, such matrices do not provide adequate control over the drug release rate, instead resulting in a release that approximates first-order kinetics.

Thus there is need to develop stable controlled release compositions of pregabalin, which provide complete drug release and afford stable plasma levels in a once-a-day dosing regimen using hydrophobic release controlling agent(s).

A further aspect of the invention provides a solid dosage form, such as a tablet, capsules pellets, granules, powders and microtablets that are adapted for once daily oral dosing.

OBJECT OF THE INVENTION

The controlled release pharmaceutical compositions comprising pregabalin of present invention may employ any pharmaceutically acceptable form of pregabalin including base or its pharmaceutically acceptable complexes, salts, polymorphs, hydrates, solvates, enantiomers or racemates.

Therefore, the first object of the present invention provides a controlled release pharmaceutical compositions comprising therapeutically effective amount of pregabalin or pharmaceutically acceptable complexes, salts, polymorphs, hydrates, solvates, enantiomers or racemates thereof wherein the composition comprises pregabalin and hydrophobic release controlling agent(s), and optionally other pharmaceutically acceptable excipients.

Yet another object of the present invention provides a controlled release pharmaceutical compositions comprising therapeutically effective amount of pregabalin or pharmaceutically acceptable complexes, salts, polymorphs, hydrates, solvates, enantiomers or racemates thereof wherein the composition comprises pregabalin and hydrophobic release controlling agent(s), and optionally a wicking agent.

Yet another object of the present invention provides a controlled release pharmaceutical compositions comprising therapeutically effective amount of pregabalin or pharmaceutically acceptable complexes, salts, polymorphs, hydrates, solvates, enantiomers or racemates thereof wherein the composition comprises pregabalin and hydrophobic release controlling agent(s), optionally a wicking agent and additionally hydrophilic rate controlling components.

Yet another object of the invention provides controlled release pharmaceutical compositions comprising pregabalin or pharmaceutically acceptable complexes, salts, polymorphs, hydrates, solvates, enantiomers or racemates thereof, comprising a core wherein said core comprises pregabalin or pharmaceutically acceptable complexes, salts, polymorphs, hydrates, solvates, enantiomers or racemates thereof, with one or more auxiliary pharmaceutical excipients and a coating layer comprising rate controlling hydrophobic and hydrophilic agent(s).

Yet another object of the present invention is to provide for controlled release pharmaceutical compositions comprising therapeutically effective amount of pregabalin or pharmaceutically acceptable complexes, salts, polymorphs, hydrates, solvates, enantiomers or racemates thereof wherein the composition comprises pregabalin and hydrophobic release controlling agent(s) thereof, in which the compositions exhibit in vitro release of pregabalin not less than about 75% after 12 hours, especially not less than about 75% after 10 hours.

Yet another object of the present invention is to provide a controlled release pharmaceutical composition comprising therapeutically effective amount of pregabalin or pharmaceutically acceptable complexes, salts, polymorphs, hydrates, solvates, enantiomers or racemates thereof wherein the composition comprises pregabalin and hydrophobic release controlling agent(s)thereof, in which the compositions exhibits in vitro release of pregabalin not less than about 55%, after 7 hours.

DETAILED DESCRIPTION OF THE INVENTION

Figure 1:
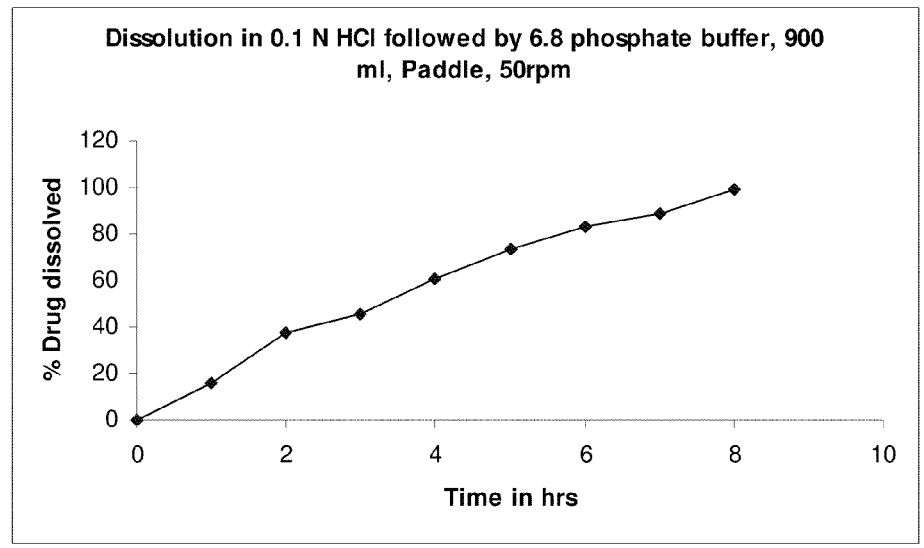
FIG. 1 shows a release profile of controlled release dosage forms of pregabalin of example 1, in Type II USP apparatus, 0.1N HCl followed by pH 6.8 phosphate buffer, 900 ml, and 50 rpm.
Figure 2:
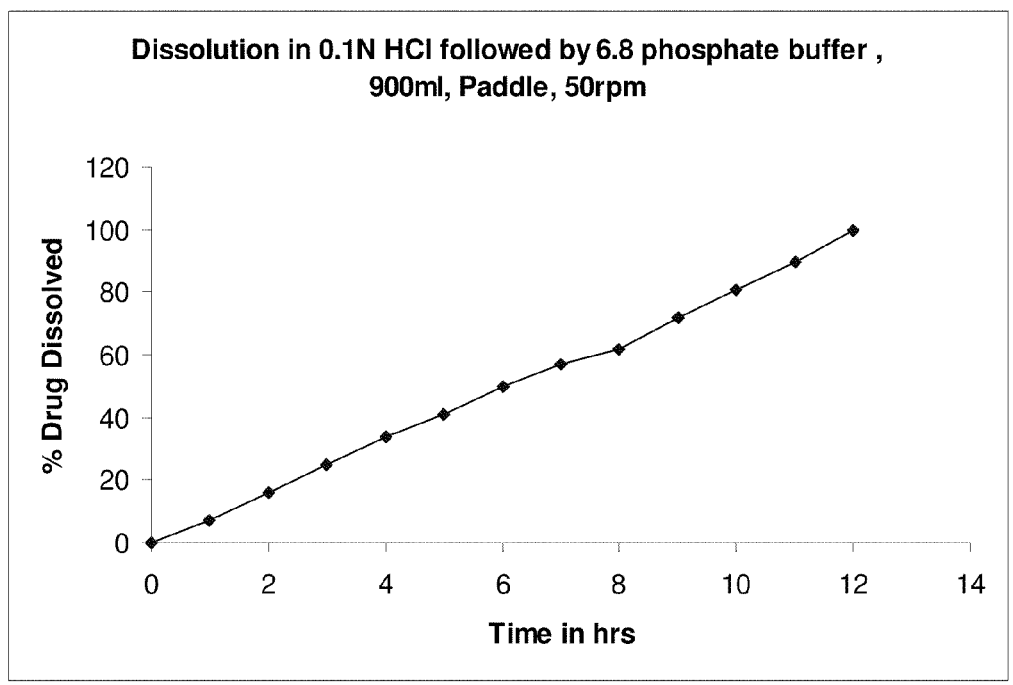
FIG. 2 shows a release profile of controlled release dosage forms of pregabalin of example 2, in Type II USP apparatus, 0.1N HCl followed by pH 6.8 phosphate buffer, 900 ml, and 50 rpm.

The dosage forms of the present invention typically contain 25 to 900 mg pregabalin as base. The dosage forms of the invention optionally may comprise pharmaceutically acceptable complexes, salts, polymorphs, hydrates, solvates, enantiomers or racemates of pregabalin. "Pharmaceutical composition" refers to the combination of one or more drug substances and one or more excipients.

"Drug product," "pharmaceutical dosage form," "dosage form," "final dosage form" and the like, refer to a pharmaceutical composition that is administered to a subject in need of treatment and generally may be in the form of tablets, capsules, sachets containing powder or granules, pellets, liquid solutions or suspensions, patches, and the like.

"About" will be understood by persons of ordinary skill in the art and will vary to some extent on the context in which the term is used If there are uses of the term which are not clear to persons of ordinary skill in the art given the context in which it is used, "about" will mean up to plus or minus 10% of the particular term.

The term "controlled release compositions" herein refers to any composition or dosage form which comprises an active drug and which is formulated to provide a longer duration of pharmacological response after administration of the dosage form than is ordinarily experienced after administration of a corresponding immediate release composition comprising the same drug in the same amount. Controlled release compositions include, inter alia, those compositions described elsewhere as "extended release", "delayed release", "sustained release", "prolonged release", "programmed release", "time release" and/or "rate controlled" compositions or dosage forms.

The term "wicking agent" is defined as any material with the ability to draw water into the network of a delivery dosage form. By so doing, a wicking agent provides enhanced flow channels for the pharmaceutical agent, which has been made predominantly into its solubilized form.

The hydrophobic release controlling agents are selected from but are not limited to polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly (ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), waxes such as beeswax, carnauba wax, paraffin wax, microcrystalline wax, and. ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, zein and hydrogenated vegetable oils or their mixtures thereof.

The hydrophilic release controlling agents are selected from but are not limited to hydroxypropyl methylcellulose (HPMC), hydroxypropyl cellulose (HPC), polyethylene oxide, polyvinyl alcohol, polyvinylpyrrolidone, xanthan gum, guar gum, chitosan and its derivatives, carbomer, carrageenan, carboxymethyl cellulose, sodium alginate, polyglycolized glycerides, polyethyleneglycol, or mixture thereof.

The wicking agents are selected from the group comprising hydrophilic, organic, polymeric, fusible substance or a particulate soluble or insoluble inorganic material. Suitable hydrophilic, organic, fusible wicking agents include polyethylene glycols (PEGs) of various molecular weights e.g. 1,000 to 20,000 preferably 4,000 to 10,000 and suitable particulate inorganic wicking agents include dicalcium phosphate and lactose. It is preferred to use a hydrophilic fusible, organic polymeric as wicking agent. Other examples of wicking agents include high HLB surfactants (for example Tween 20, Tween 60 or Tween 80; ethylene oxide propylene oxide block copolymers, ionic surfactants such as sodium lauryl sulfate, sodium docusate, non-swelling hydrophilic polymers such as cellulose ethers, complexing agents such as: polyvinyl pyrrolidone, cyclodextrins and non-ionic surface active agents; and micelle forming agents, which may be surface active agents such as Tweens (Poly(ethylene Oxide) modified sorbitan monoesters), Spans (fatty acid sorbitan esters), sodium lauryl sulfate and sodium docusate.

The term "controlled release pharmaceutical compositions" includes a pharmaceutical composition that encompasses one or more individual units. The units may be a capsule or tablet or may be in form of granules, pellets, minitablets or beads.

The compositions of the present invention can also include other materials such as binders, diluents, anti-adherents, glidants and lubricants.

Diluents may be, for example, any pharmaceutically acceptable, non-toxic diluent. Particular examples include lactose, dextrose, sucrose, maltose, microcrystalline cellulose, starch, calcium hydrogen phosphate, mannitol and the like.

Binders may be, for example, starch, sugars, gums, low molecular weight hydroxypropyl methylcellulose, povidone, hydroxypropyl cellulose, hydroxyethyl cellulose or the like.

Lubricants may be, for example, talc, magnesium stearate, calcium stearate, stearic acid, sodium stearyl fumarate, sodium benzoate or the like.

Antiadherents and Glidants may be, for example, colloidal silicon dioxide, talc or the like.

Solid oral dosage forms of the present invention may be prepared by any conventional techniques for example dry granulation, direct compression, wet granulation, melt granulation and extrusion-spheronization.

EXAMPLES

The following examples are intended to be illustrative and non-limiting:

Example: 1

| Sr. No. | Ingredient | Mg/Unit dose |
|---|---|---|
| | CORE | |
| 1. | Pregabalin | 75.00 |
| 2. | Microcrystalline Cellulose (Avicel PH 101) | 73.00 |
| 3. | HPMC E5 | 2.00 |
| 4. | Purified Water | Q.S. |
| | Total: | 150.00 |
| | EXTENDED RELEASE COATING | |
| 1. | Ethyl Cellulose (N50) | 9.80 |
| 2. | HPMC E5 | 4.20 |
| 3. | Triethyl Citrate | 1.40 |
| 4. | Talc | 4.60 |
| 5. | Isopropyl Alcohol | 80.00 |
| 6. | Dichloromethane | 320.00 |
| | Total Weight | 170.00 mg |

Brief Manufacturing Procedure:
1. Mix Pregabalin with Microcrystalline Cellulose and sift them through a suitable sieve and load the blend in RMG.
2. Prepare HPMC E5 solution in suitable quantity of water.
3. Granulate the blend of step 1 with binder solution of step 2.
4. Extrudate the wet mass through 1 mm sieve using extruder and spheronize using spheronizer.
5. Dry the pellets at a suitable temperature in FBD and size them to suitable fractions.
6. Disperse Ethyl cellulose, HPMC E5, Triethylcitrate and Talc in the Isopropyl alcohol and Dichloromethane solution.
7. Coat pellets with the above coating composition in FBP to get the build up of approximately in a range of 12-18% to get the desired profile.
8. The coated pellets can either be filled in the capsules or compressed as tablets.

Example: 2

| Sr. No. | Ingredient | Mg/Unit dose |
|---|---|---|
| | CORE | |
| 1. | Pregabalin | 75.00 |
| 2. | Hydrogenated Vegetable Oil | 93.00 |
| 3. | Magnesium Stearate | 2.00 |
| | Total: | 170.00 mg |

Brief Manufacturing Procedure:
1) Mix Pregabalin and Hydrogenated Vegetable Oil material at suitable temperature with continuous stiffing.
2) Maintain the temperature of the melt mass for a sufficient period of time.
3) Cool the melted mass at room temperature until a hard mass is obtained.
4) Sift the mass through a suitable sieve.
5) Store the final granules in a well-closed container.
6) These granules can either be filled in the capsules or compressed as tablets.

Example: 3

| Sr. No. | Ingredient | Mg/Unit dose |
|---|---|---|
| | CORE | |
| 1. | Pregabalin | 150.00 |
| 2. | Lactose monohydrate | 128.00 |
| 3. | Ethylcellulose | 40.00 |
| 4. | Isopropyl Alcohol | Q.S. |
| 5. | Colloidal silicon dioxide | 11.60 |
| 6. | Talc | 6.40 |
| 7. | Magnesium Stearate | 4.00 |
| 8 | Total Weight | 340.00 mg |

Brief Manufacturing Procedure:
1. Mix Pregabalin with Lactose monohydrate, Ethyl cellulose, Colloidal silicon dioxide and Talc in a suitable blender.
2. Lubricate the blend with Magnesium stearate.
3. The above lubricated blend is compressed into tablets.

Example: 4

| Sr. No. | Ingredient | Mg/Capsule |
|---|---|---|
| | CORE | |
| 1. | Pregabalin | 75.00 |
| 2. | Lactose monohydrate | 50.00 |
| 3. | Starch | 14.00 |
| 4. | Purified Water | Q.S. |

7 -continued

| Sr. No. | Ingredient | Mg/Capsule |
|---|---|---|
| 5. | Aerosil | 4.00 |
| 6. | Talc | 4.00 |
| 7. | Magnesium Stearate | 3.00 |
| | Total | 150.00 |
| | EXTENDED RELEASE COATING | |
| 1. | Ethyl Cellulose (N50) | 9.80 |
| 2. | HPMC E5 | 4.20 |
| 3. | Triethyl Citrate | 1.00 |
| 4. | Talc | 5.00 |
| 5. | Isopropyl Alcohol | 80.00 |
| 6. | Dichloromethane | 320.00 |
| | Total Weight | 170.00 mg |

1. Mix Pregabalin with Lactose monohydrate, Starch and load the blend in RMG.
2. Granulate the powder mass of step 1 with suitable quantity of water.
3. Sift the above granulated mass through a suitable sieve.
4. Dry the granules in suitable dryer.
5. Lubricate the dried granules with aerosil, talc and magnesium stearate.
6. Compress the above blend into minitablets or into a single tablet.
7. Disperse Ethyl cellulose, HPMC E5, Triethylcitrate and Talc in the Isopropyl alcohol and Dichloromethane solution.
8. Coat tablet or minitablet with the solution of step 7 to get the build up of approximately in a range of 10-18% to get the desired profile.
9. Alternatively the coated Minitablets can be filled into a capsule of suitable size.

Example: 5

| Sr. No. | Ingredient | Mg/Capsule |
|---|---|---|
| | CORE | |
| 1. | Pregabalin | 75.00 |
| 2. | Lactose monohydrate | 40.00 |
| 3. | Starch | 8.00 |
| 4. | Microcrystalline cellulose | 20.00 |
| 4. | Aerosil | 4.00 |
| 5. | Magnesium Stearate | 3.00 |
| | Total | 150.00 |

8 -continued

| Sr. No. | Ingredient | Mg/Capsule |
|---|---|---|
| | EXTENDED RELEASE COATING | |
| 1. | Ethyl Cellulose (N50) | 9.80 |
| 2. | HPMC E5 | 4.20 |
| 3. | Triethyl Citrate | 1.00 |
| 4. | Talc | 5.00 |
| 5. | Isopropyl Alcohol | 80.00 |
| 6. | Dichloromethane | 320.00 |
| | Total Weight | 170.00 mg |

1. Mix Pregabalin with Lactose monohydrate, Starch and Microcrystalline cellulose
2. Lubricate the dried granules with aerosil and magnesium stearate.
3. Compress the above blend into minitablets or into a single tablet.
4. Disperse Ethyl cellulose, HPMC E5, Triethylcitrate and Talc in the Isopropyl alcohol and Dichloromethane solution.
5. Coat tablet or minitablet with the coating solution of Step 4 to get the build up of approximately in a range of 12-18% to get the desired profile.
6. Coated Minitablets can be filled into a capsule of suitable size.

The invention claimed is:

1. A controlled release pharmaceutical composition comprising therapeutically effective amount of pregabalin or salts thereof as active ingredient, a hydrophobic release controlling agent consisting essentially of ethyl cellulose and optionally other pharmaceutically acceptable excipients wherein said composition exhibits an in vitro release of the pregabalin or salts thereof of not less than about 55% after 7 hours.

2. The pharmaceutical composition of claim 1, wherein the composition is in the form of capsules, tablets, or multilayer tablets.

3. A controlled release pharmaceutical composition consisting essentially of a therapeutically effective amount of pregabalin or salts thereof as active ingredient and a hydrophobic release controlling agent consisting essentially of hydrogenated vegetable oil and optionally other pharmaceutically acceptable excipients wherein said composition is prepared by melt granulation, and wherein said composition exhibits an in vitro release of the pregabalin or salts thereof of not less than about 75% after 12 hours.

4. The composition of claim 1 comprising at least one pharmaceutically acceptable excipient selected from binders, diluents, glidants, lubricants, and combinations thereof.

5. The composition of claim 2 comprising at least pharmaceutically acceptable excipient selected from binders, diluents, glidants, lubricants, and combinations thereof.

6. The pharmaceutical composition of claim 3, wherein the composition is in the form of capsules, tablets, granules, pellets or beads.

* * * * *